United States Patent
Dysarz (10) Patent No.: US 6,585,701 B1
(45) Date of Patent: *Jul. 1, 2003

(54) TRAP IN MODULAR HUB CHAMBER SPRING NEEDLE CANNULA

(76) Inventor: Edward D. Dysarz, 11423 Triola La., Houston, TX (US) 77072

( * ) Notice: Subject to any disclaimer, the term of this patent is extended or adjusted under 35 U.S.C. 154(b) by 0 days.

This patent is subject to a terminal disclaimer.

(21) Appl. No.: 09/097,571

(22) Filed: Jun. 15, 1998

(51) Int. Cl.[7] .......................... A61M 5/00; A61M 5/32; A61M 5/178
(52) U.S. Cl. ...................... 604/263; 604/195; 604/198; 604/239; 604/164.11; 128/919
(58) Field of Search ................................ 604/181, 187, 604/195, 198, 192, 263, 264, 272, 110, 239, 158, 164.01–164.02, 164.06, 164.09, 164.11, 523, 533–34; 128/917, 919

(56) References Cited

U.S. PATENT DOCUMENTS

| | | |
|---|---|---|
| 3,008,570 A | 11/1961 | Roehr et al. |
| 3,107,785 A | 10/1963 | Roehr |
| 3,306,291 A | 2/1967 | Burke |
| 3,703,174 A * | 11/1972 | Smith ......................... 221/278 |
| 3,895,633 A | 7/1975 | Bartner et al. |
| 4,300,678 A | 11/1981 | Gyure et al. |
| 4,356,822 A | 11/1982 | Winstead-Hall |
| 4,425,120 A | 1/1984 | Sampson et al. |
| 4,639,249 A | 1/1987 | Larson |
| 4,655,751 A | 4/1987 | Harbaugh |
| 4,664,654 A | 5/1987 | Strauss |
| 4,838,863 A * | 6/1989 | Allard et al. ................ 604/110 |
| 4,894,055 A * | 1/1990 | Sudnak ......................... 604/110 |
| 4,946,446 A * | 8/1990 | Vadher ......................... 604/198 |
| 5,088,986 A * | 2/1992 | Nusbaum ..................... 604/195 |
| 5,201,710 A | 4/1993 | Caselli |
| 5,246,428 A * | 9/1993 | Falknor ....................... 604/198 |
| 5,405,376 A * | 4/1995 | Mulier et al. ................ 604/272 |
| 5,575,777 A * | 11/1996 | Cover et al. ................. 604/110 |
| 5,755,696 A * | 5/1998 | Caizza ................... 604/164.11 |
| 5,843,034 A | 12/1998 | Redfern |
| 5,921,960 A | 7/1999 | McGary |
| 5,935,104 A | 8/1999 | Janek |
| 5,935,113 A * | 8/1999 | Dysarz ........................ 604/263 |
| 6,036,674 A | 3/2000 | Caizza |

FOREIGN PATENT DOCUMENTS

| | | | | |
|---|---|---|---|---|
| SU | 0362618 | * | 12/1972 | ................. 604/239 |
| SU | 0520103 | * | 7/1976 | ................. 604/272 |

* cited by examiner

Primary Examiner—Jeffrey R. Jastrzab
Assistant Examiner—Patricia M. Bianco
(74) Attorney, Agent, or Firm—Streets & Steele; Jeffrey L. Streets (57) ABSTRACT

A retractable needle cannula module for connecting to a conventional syringe has a biased spring needle cannula. The spring needle cannula is biased and locked to prevent the spring needle cannula from pulling the needle into the hub chamber. After medicament has been injected into a body, the spring needle cannula is released and trapped inside the hub chamber.

24 Claims, 6 Drawing Sheets

TRAP IN MODULAR HUB CHAMBER SPRING NEEDLE CANNULA

BACKGROUND OF THE INVENTION

There are many safety syringe designs available today. Some of these designs have a sleeve or a sheath that will cover the needle after it has been used. Some typical designs with sleeves or sheaths are Z. M. Roehr et al U.S. Pat. No. 3,008,570, Z. M. Roehr U.S. Pat. No. 3,107,785, Bartner, et al U.S. Pat. No. 3,895,633, G K Burke U.S. Pat. No. 3,306,291, Gyure et al U.S. Pat. No. 4,300,678, Winstead Hall U.S. Pat. No. 4,356,822, Sampson et al U.S. Pat. No. 4,425,120, Larson U.S. Pat. No. 4,639,249, Harbaugh U.S. Pat. No. 4,655,751, Strauss U.S. Pat. No. 4,664,654, Spencer U.S. Pat. No. 4,702,738, Milorad U.S. Pat. No. 4,702,739, Spencer U.S. Pat. No. 4,801,295, Poncy U.S. Pat. No. 4,815,022, and Hughes U.S. Pat. No. 4,840,619.

Other designs have a retractable needle such as Weltman U.S. Pat. No. 3,306,290, and Dent U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis, or other diseases from an accidental injection with a contaminated needle into others after the needle of the syringe has been inserted into a patient with the above mentioned diseases. These various designs all work well up to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the syringe the person holding the syring in one hand may be bumped and accidentally inject the needle into their other hand before it can grasp the syringe. Other accidental jabbing or injections can happen in an ambulance just as a person tries to grasp the syringe with a contaminated needle, the ambulance can hit a bump in the road causing the person holding the syringe to accidentally stick another person or themselves with the contaminated needle. The need has developed for a syringe that will cover the contaminated needle with the use of only one hand.

All of these designs also combine the needle cannula with the syringe and therefore create a storage problem. At present, needle cannulas are fixed to the hub but not to the syringe so that a variety of lengths and guages of needle cannulas are stored in one locker or storage cabinet which may contain about twenty various lengths and gauges of needle cannulas; an inventory of about twenty or more of each guages and lengths of needle cannulas may be stored in each section. There may also be about ten sizes of syringes with about twenty or more of each syringe stored in the same locker. When a given quantity of a given medicament is required, the proper size of needle cannula is fitted to the proper syringe thereby combining the right length and guage of needle cannula with the right size of syringe.

All of the above inventions would require an inventory ten times of that of the present invention. Each needle cannula size would have to be fixed to each syringe size and each syringe size would have to be fixed to each needle cannula size and this would be hundreds of needle cannula syringe combinations which would be multiplied by ten each; the numbers required for the necessary inventory in a given floor of a hospital would be astronomical. The need has developed for a safety needle cannula that would be a module apart from the syringe.

SUMMARY

It is the object of this invention is to provide a needle cannula wherein the needle that is used is independent of the syringe and is retracted into the modual hub chamber and protects others from an accidental pricking after the needle cannula has been used, the needle can be retracted into the modual hub chamber with the use of only one hand and that one hand being the hand that was used to inject the needle into the patient.

Another object of the present invention is to render the needle cannula useless after the needle cannula is retracted into the modual hub chamber and to further prevent the reuse and abuse by users of illicit drugs.

It is still another object of the present invention to further prevent the accidental release of the needle cannula after the needle cannula is in the hub chamber.

It is still yet another object of the present invention to provide a safety needle cannula without modifying the syringe.

The foregoing and other objects and advantages are attained by a spring needle cannula, a hub chamber, a hub to fix the device to a standard syringe, an inclined plane latching means and a latch release means wherein when said needle cannula is used to inject a drug, medicament, or other material into a body the latch release means is activated and the coiled spring cannula withdraws the distal end of said spring needle cannula into the hub chamber rendering the spring needle cannula harmless to prevent the accidental pricking of others and to prevent the contaminated spring needle cannula from being removed from the hub chamber.

The features of the present invention can be best understood together with further objects and advantages by reference to the following descriptions when taken in connection with accompanying drawings, wherein like numerals indicate like parts.

DETAILED DESCRIPTION OF THE PREFERED EMBODIMENTS

Figure 1:
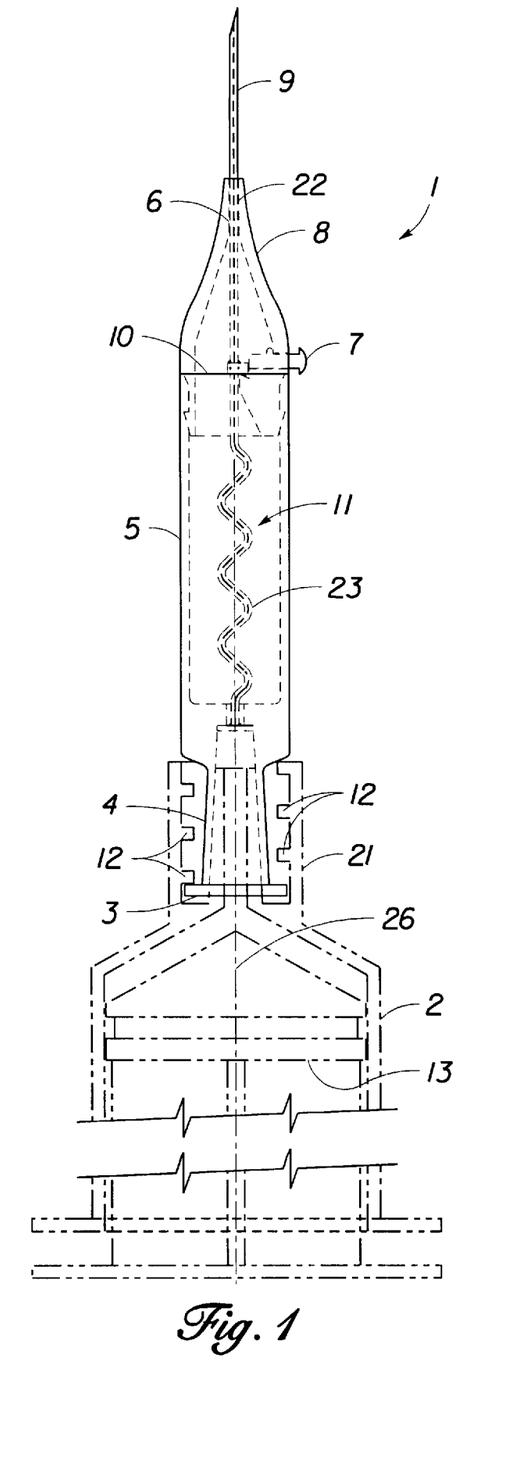
FIG. 1   Is an elevation view of the device fixed to the syringe.

Refering to FIG. 1 there is shown an elevation view if the modular assembly device 1 of the first preferred embodiment.

The modular assembly device 1 is shown as the first preferred embodiment, is a modular assembly suitably fixed to the threads 12 inside of the threaded extention 21 of typical syringe 2 in a conventional manner. This type of threaded extension 21 is often referred to as a Luer-Lok tip however the tip could be a slip tip, an eccentric tip or a catheter tip by design choice. The threaded extension 21 is part of a typical or conventional syringe 2. The syringe 2 is shown with a plunger 13 for reference only. The modular assembly device 1 as shown is fixed to any conventional or typical syringe 2 without any modifications required to the syringe 2. The modular assembly device 1 will interface with any existing syringe by design choice.

The cannula distal end 9 is shown extending from the hub chamber cap tip 22 at the first end of the hub chamber cap 8, through the hub tunnel 6. The second end of the hub chamber cap 8 is shown suitably fixed to the first end of the hub chamber with a snap on the interface connection referred to as the hub joint 10. The cannula release button 7 is shown extending from the hub chamber cap 8, however, it could also be shown extending from the hub chamber by design choice. The spring needle cannula 11 distal end 9 extends into the hub chamber 5 wherein the spring needle cannula 11 is formed into coils 23.

The proximal end of the spring needle cannula 11 is shown suitably fixed to the first end of the hub 4. The first side of the threaded flange 3 is shown at the second end of the hub 4. The second side of the threaded flange is near the syringe 2. The threaded flange 3 is shown threaded or suitably fixed to the internal threads 12 that are on the inside of the threaded extension 21 that is at the first end of the syringe 2. A centerline 26 is shown that extends from the distal end of the spring needle cannula 11 to the second end of the syringe to transfer medicament from a syringe 2. The modular assembly device is used as a conduit to transfer medicament from a syringe 2 and dispose said medicament into a body.

Figure 2:
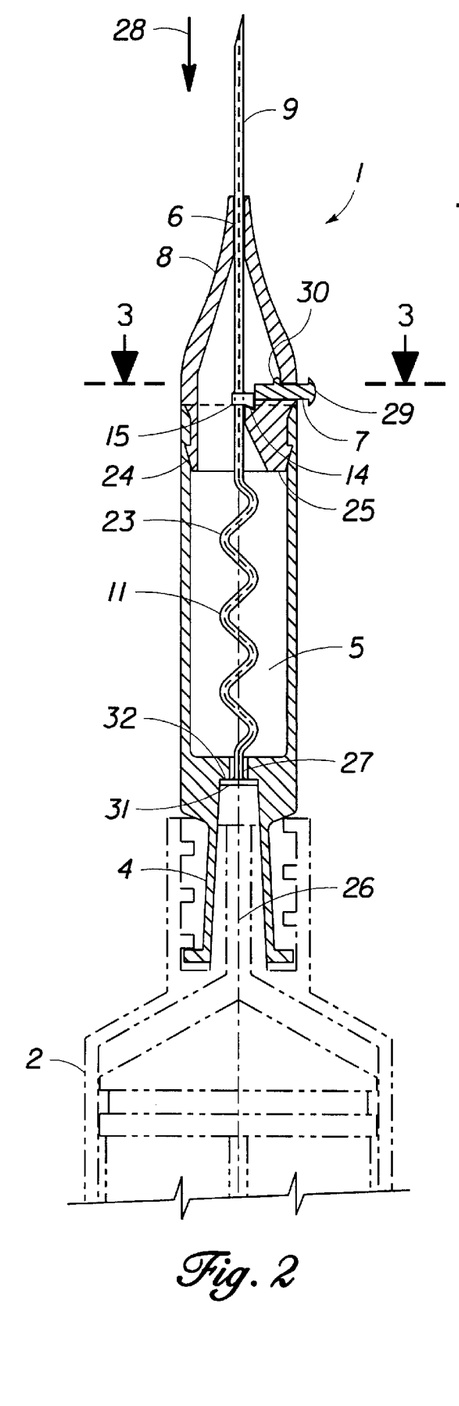
FIG. 2   Is an enlarged section elevation of the device fixed to a syringe.

Refering to FIG. 2 there is shown an enlarged section elevation of the modular assembly device 1 suitably fixed to the syringe 2. The cannula distal end 9 is shown extending from the hub tunnel 6 of the hub chamber 5. The hub chamber cap 8 is shown suitably fixed to the hub chamber 5 with a snap on connection 24 that could also use adhesive to make up the connection by design choice.

The latch foundation 25 is shown formed on the inside of the hub chamber cap 8 and extends toward the centerline 26 of the device 1. An inclined plane latch 14 is shown formed on the latch foundation 25. Part of the cannula push out hook 15 is shown hooked onto the inclined plane latch 14. The cannula push out hook 15 is shown suitably fixed to the spring needle cannula 11 by adhesive or other suitable means. The spring needle cannula 11, is disposed in a hole formed in the cannula push out hook 15 wherein the hole extends from the first side to the second side of the cannula push out hook 15 wherein the spring needle cannula is disposed in the hole formed in the cannula push out hook 15. The third side of the cannula push out hook 15 is shown with a second inclined plane that will correspond with the first inclined plane of the inclined plane latch 14. The cannula push out hook 15 is held in place in the inclined plane latch 14 by the tension caused by the coils 23 formed near the proximal end 27 of the spring needle cannula 11. The coils 23 shown in FIGS. 1 and 2 are biased coils. The cannula push out hook 15 that is held in place in the inclined plane latch 14 further prevents the cannula distal end 9 from being thrust back (arrow 28) when the spring needle cannula 11 is inserted into a body.

The cannula release button 7 is shown near the incline plane latch 14 and is disposed in a hole formed in the hub chamber cap 8 that extends from the outside to the inside of the hub chamber 8. The cannula release button 7 is shown with a second knob 30 fixed to the third end of the cannula release button 7 to further prevent the cannula release button 7 from being removed or from falling out of the hole formed in the hub chamber cap 8. The first knob 29 is shown at the first end of the cannula release button 7 wherein when the cannula release button 7 is depressed it will disegage the cannula push out hook 15 from the inclined plane latch 14.

A flange 31 is show suitably fixed to the proximal end 27 of the spring needle cannula 11 by welding, adhesive, or some other suitable means by design choice. The flange 31 is held in place in a ridge 32 formed on the inside of the second end of the hub chamber 5. The hub 4 is shown suitably attached to the syringe 2. The hub chamber 5 is integral with the hub 4. The hub 4 could also be a slip on hub by design choice.

Figure 3:
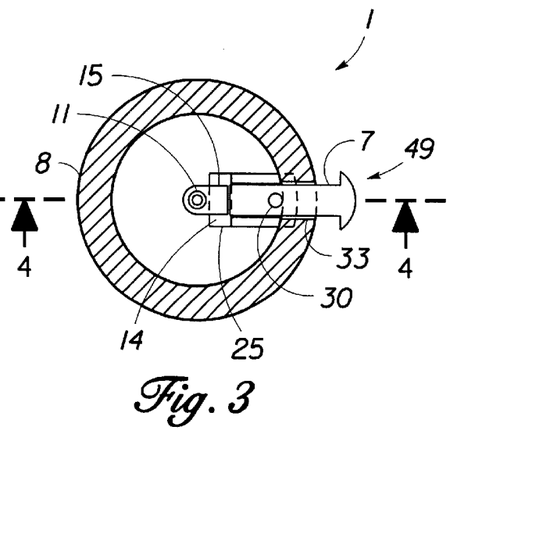
FIG. 3   Is an enlarged section elevation as taken through FIG. 2.

Referring to FIG. 3 there is shown a section elevation of the modular assembly device 1 as taken through FIG. 2.

The hub chamber cap 8 is shown with a hub chamber cap hole 33 wherein the cannula release button 7 is disposed in the hub chamber cap hole 33. The second end of the cannula release button 7 is shown near the third end of the cannula push out hook 15. The cannula push out hook 15 is further being held in place by the combination of the tension of the spring needle cannula 11 and the inclined plane latch 14; the inclined plane latch 14 is formed on the latch foundation 25 wherein the latch foundation 25 is shown near the cannula release button 7. The second knob 30 is seen on the cannula release button 7.

Figure 4:
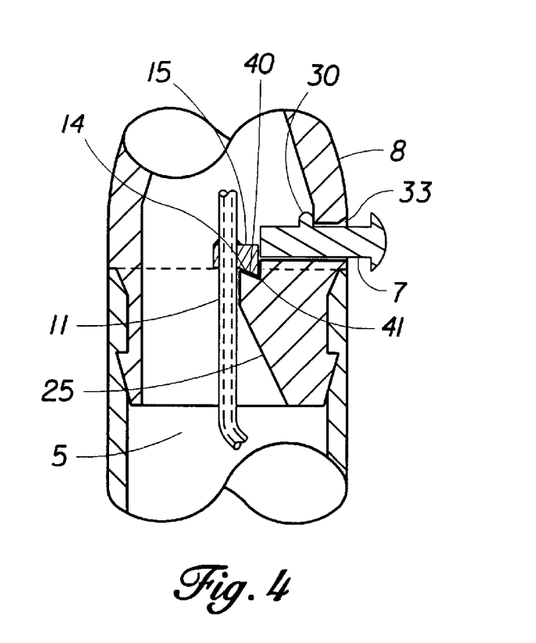
FIG. 4   Is a section elevation as taken through FIG. 3.

Refering to FIG. 4 there is shown an enlarged section elevation of the inclined plane latch 14 and the cannula push out hook 15.

The cannula push out hook 15 with the first inclined plane 40 is shown locked or held in the inclined plane latch 14 with the second inclined plane 41 that is formed in the latch foundation 25. To release the cannula push out hook 15, the cannula release button 7 must be pushed by a finger or thumb. The cannula push out hook 15 is retained from moving out because the spring needle cannula 11 is pulling the cannula push out hook 15 in the direction of the cannula release button 7. The cannula release button 7 is prevented from being pushed out of the hub chamber 5 or the hub chamber cap 8 by the second knob 30 that is pressing on the inside surface of the hub chamber cap 8.

The hub chamber cap hole 33 is shown formed in the hub chamber cap 8 wherein the hub chamber cap hole 33 extends from the inside surface to the outside surface of the hub chamber cap 8.

Figure 5:
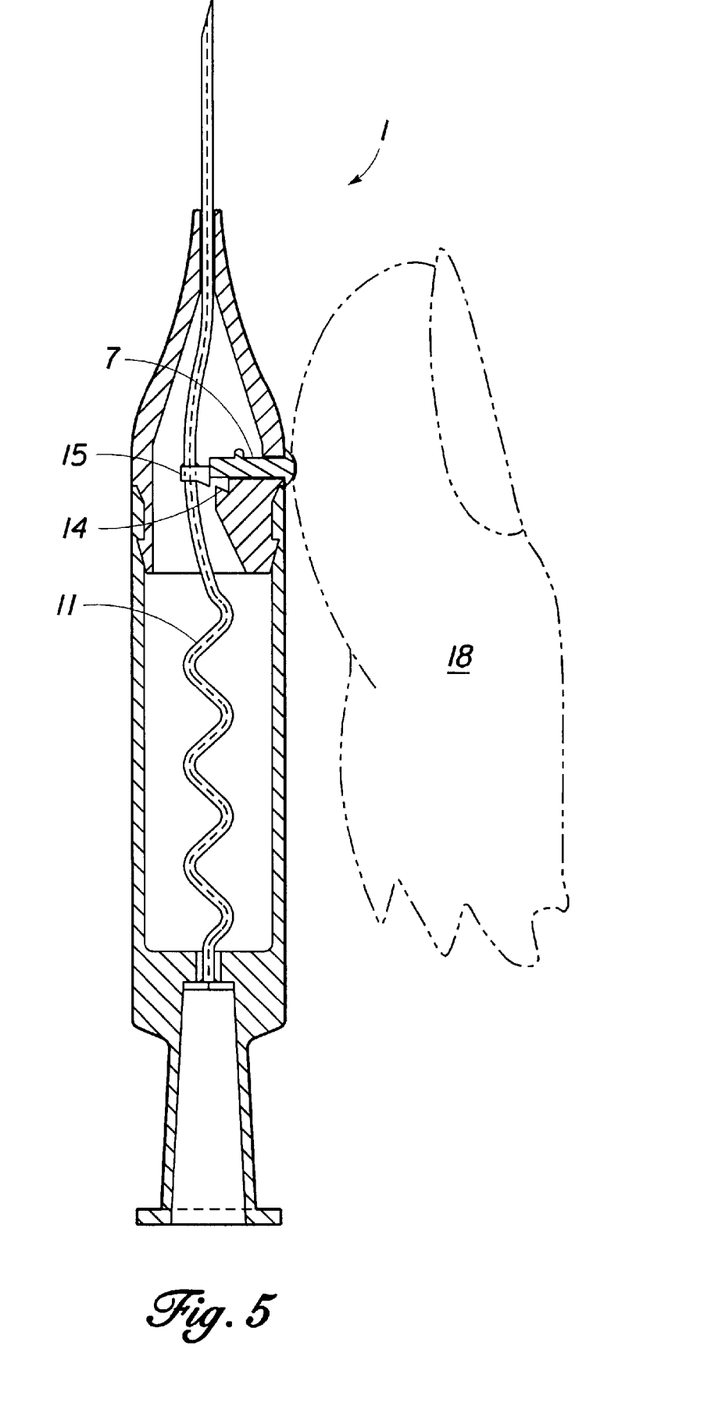
FIG. 5   Is a section elevation view of the latch means being disengaged.

Referring to FIG. 5 there is shown a section elevation view of the cannula push out hook 15 being released from the inclined plane latch 14.

The cannula release button 7 is shown being pushed by a finger 18 or a thumb wherein the second end of the cannula release button 7 pushes the cannula push out hook 15 out and away from the inclined plane latch 14. The spring needle cannula 11 is shown bending and is resisting the thrust of the cannula release button 7.

Although the syringe is not shown in FIG. 5 it should be assumed that the modular assembly device 1 is still fixed to the syringe as in FIG. 1 and FIG. 2 however, the operation to disarm or to release the spring needle cannula 11 could take place with the modular assembly device 1 fixed to the syringe or with the modular assembly device 1 removed from the syringe. The ability to release the spring needle cannula 11 does not in any way depend on the syringe.

Figure 6:
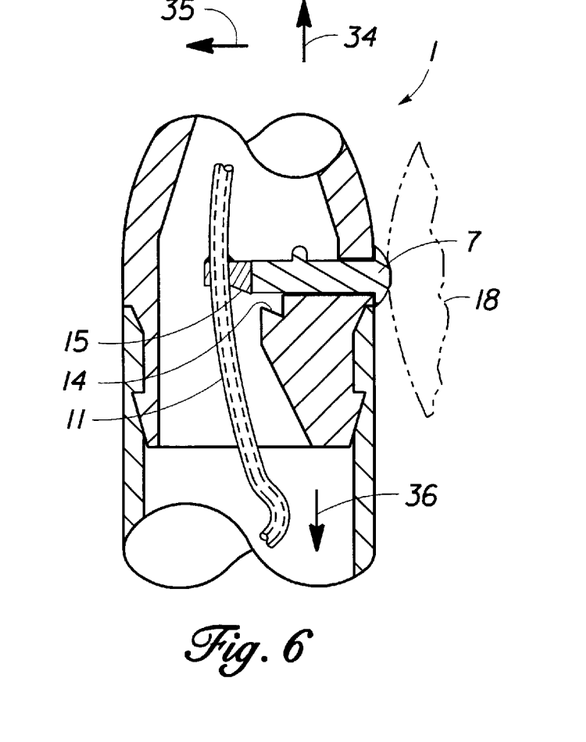
FIG. 6   Is an enlarged section elevation of the latch means being disengaged.

Referring to FIG. 6 there is shown an enlarged section elevation cannula push out hook 15 being released from the inclined plane latch 14.

The cannula release button 7 is shown being pushed by a finger 18 or a thumb wherein the second end of the cannula release button 7 thrusts on the third end of the cannula push out hook 15 and thus pushes the cannula push out hook 15 out and away from the inclined plane latch 14.

As the cannula push out hook 15 is pushed away from the inclined plane latch 14 the cannula push out hook 15 moves some in the first end direction 34 due to the incline plane of both the inclined plane latch 14 and the inclined plane of the cannula push out hook 15. The cannula push out hook 15 also moves in the centerline direction 35. The location of the cannula push out hook 15 relative to the incline plane latch 14 as shown in FIG. 6 should last but a brief moment because the coils of the spring needle cannula 11 will pull the cannula push out hook 15 in a hub direction 36.

Figure 7:
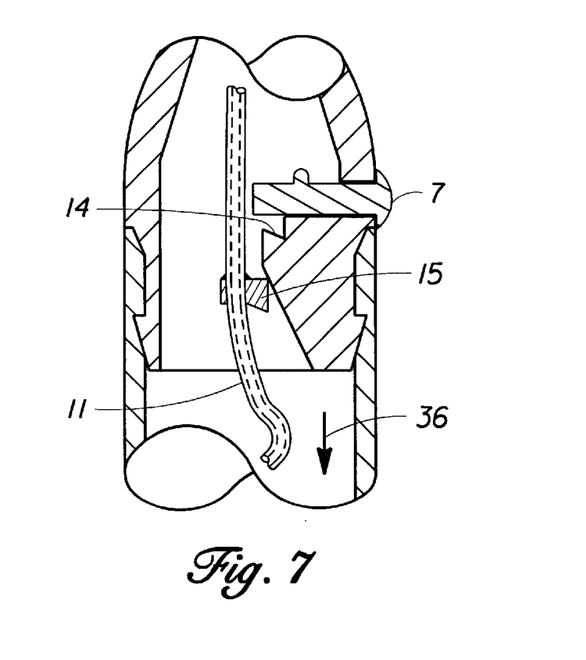
FIG. 7   Is a section elevation of the latch means disengaged.

Referring to FIG. 7 there is shown a section elevation view of the cannula push out hook 15 and the spring needle cannula 11 moving in the hub direction 36.

The cannula release button 7 has pushed the cannula push out hook 15 past the second end of the inclined plane latch 14 and now the cannula push out hook 15 is being pulled in the hub direction 36 by the coil formed on the second end of the spring needle cannula 11. This view is only going to last about an instant.

Figure 8:
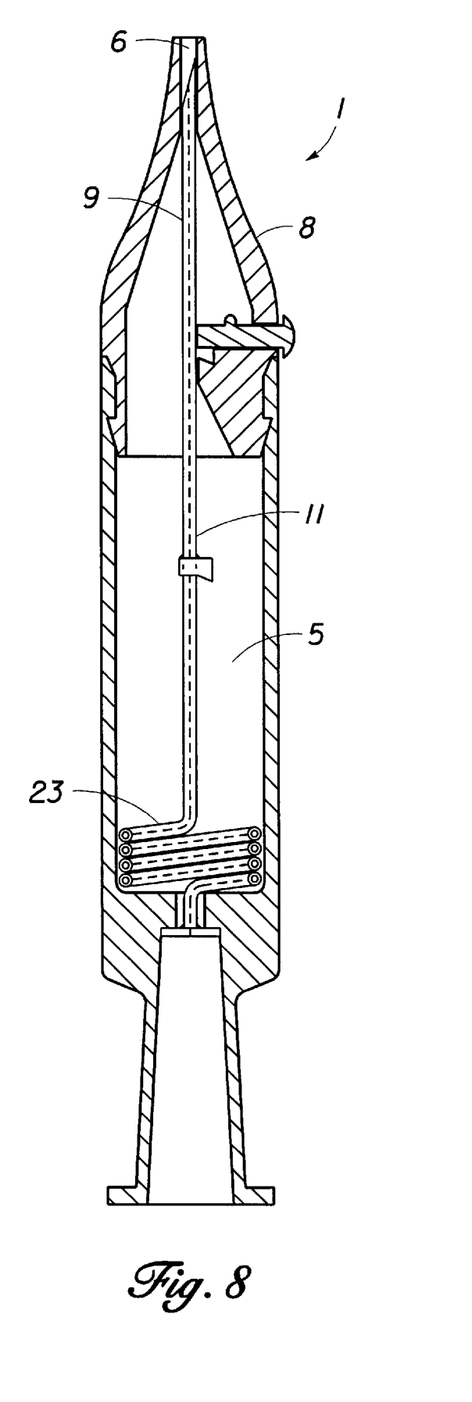
FIG. 8   Is a section elevation view of the device with the spring needle cannula contained in the hub chamber.

Referring to FIG. 8 there is shown a section elevation of the modular assembly device 1 after the coils 23 have pulled the spring needle cannula 11 into the inside of the hub chamber 5, thus the needle cannula is trapped in the modular hub chamber.

The cannula distal end 9 has been pulled into the hub tunnel 6, the hub chamber cap 8 and into the hub chamber 5 wherein it will be constantly held by the coils 23 and therefore will be prevented from extending past the hub tunnel 6 and will be unable to prick or otherwise injure anyone.

Figure 9:
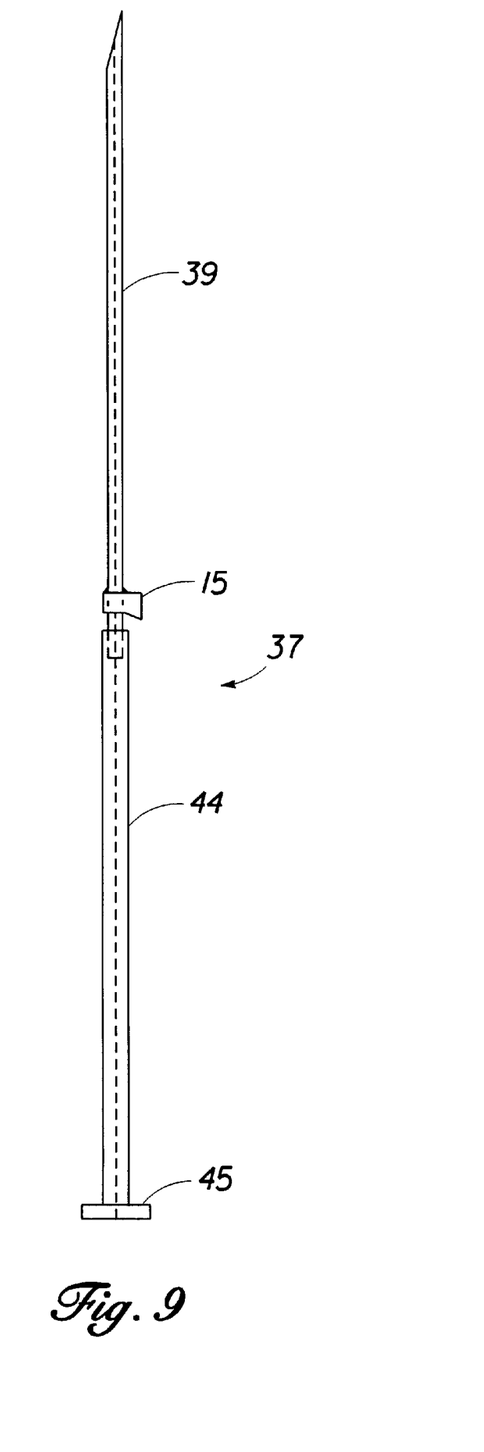
FIG. 9   Is an elevation view of a composite spring needle cannula that is comprised of two tubes fixed together.

Referring to FIG. 9 there is shown an elevation view of a composite spring needle cannula 37.

The purpose of the composite spring needle cannula 37 is to allow for a greater diameter cannula in the area of the spring cannula 44 wherein the spring cannula 44 will not crimp during the manufacturing and coiling process. Another purpose of the composite spring needle cannula 37 is to have one grade of steel for the skin penetration cannula 39 or rigid needle cannula that may be more suitable for skin penetration and another grade of steel for the coil that may be more suitable for coiling and spring conditions. A third purpose of the composite spring needle cannula 37 is to allow the skin penetration cannula 39 or rigid needle cannula, to be made out of steel while the spring cannula 44 may be made out of plastic and some other suitable material by design choice.

The first end of the composite spring needle cannula 37 is comprised of skin penetration cannula 39 or a rigid needle cannula that will penetrate skin or any other part of the body. A cannula push out hook 15 is shown suitably fixed near the second end of the skin penetration cannula 39 or rigid needle cannula by welding or by adhesive by design choice. The first end of the rigid needle cannula 37 has a suitable point formed.

The second end of the skin penetration cannula 39 or the rigid needle cannula is shown suitably fixed to the first end of the spring cannula 44. The spring cannula 44 is shown in a biased position as it would be contained in a hub chamber, the spring cannula 44 is shown suitably fixed to a flange 45 that will be fixed to a hub or hub ridge.

Figure 10:
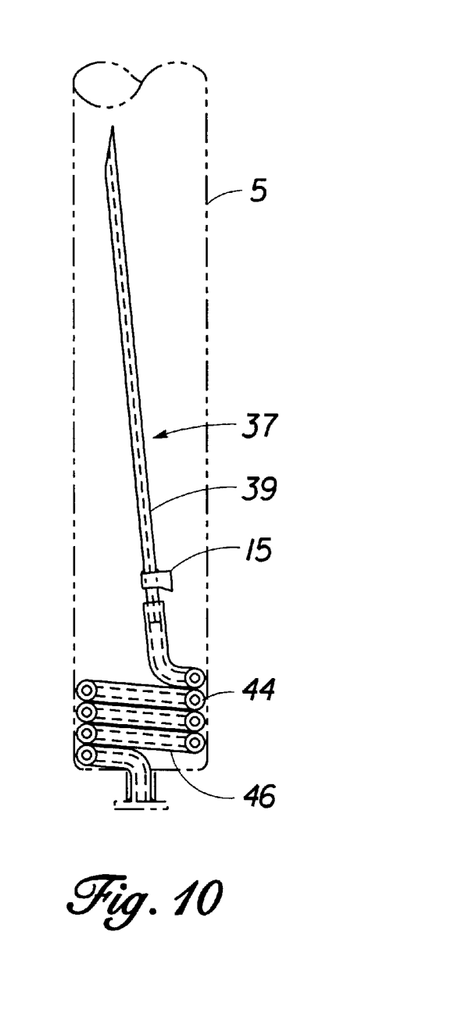
FIG. 10  Is a section elevation of the composite spring needle cannula retracted.

Referring to FIG. 10 there is shown a section elevation of the composite spring needle cannula 37 that has been released and coiled.

The spring coils 46 are formed after the cannula push out hook has been released. The skin penetration cannula 39 may remain straight and rigid or it may bend some, however, the spring cannula 44 will form into spring coils 46 and is no longer biased. The total composite spring needle cannula 37 will be pulled into the hub chamber 5 or the hub chamber cap 8.

Figure 11:
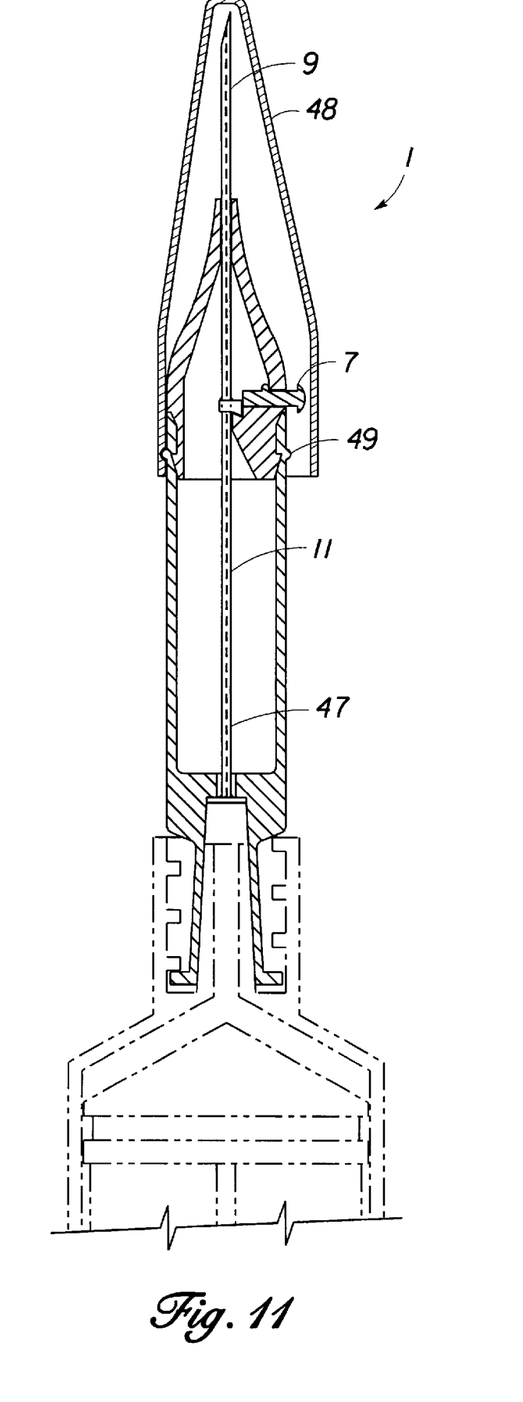
FIG. 11  Is a section elevation of a modular device wherein the spring needle cannula has been pulled into a straight or almost straight line.

Referring to FIG. 11 there is shown a section elevation view of a biased spring needle cannula 47 that has been essentially pulled straight thereby reducing the distance that the medicament has to travel and further reducing the quantity of medicament that will remain in the biased spring needle cannula 47 after the medicament has been injected into a body.

All of the components that are shown in FIG. 1 and FIG. 2 are the same in FIG. 11 only the spring needle cannula 11 has been pulled straight and therefore takes up less space both before the needle cannula 11 has been retracted and after the spring needle cannula 11 has been retracted.

The only component that has been added to the modular assembly device 1 of FIG. 11 is the cannula cap 48 has been added to FIG. 11 to cover the cannula release button 7 and the cannula distal end 9 during packaging and handling, thereby preventing the cannula release button 7 from being pressed, and thereby releasing the spring needle cannula 11 prior to use. The cap is shown with a first end and a second end, an inside surface and an outside surface and with a snap on ring 49.

Figure 12:
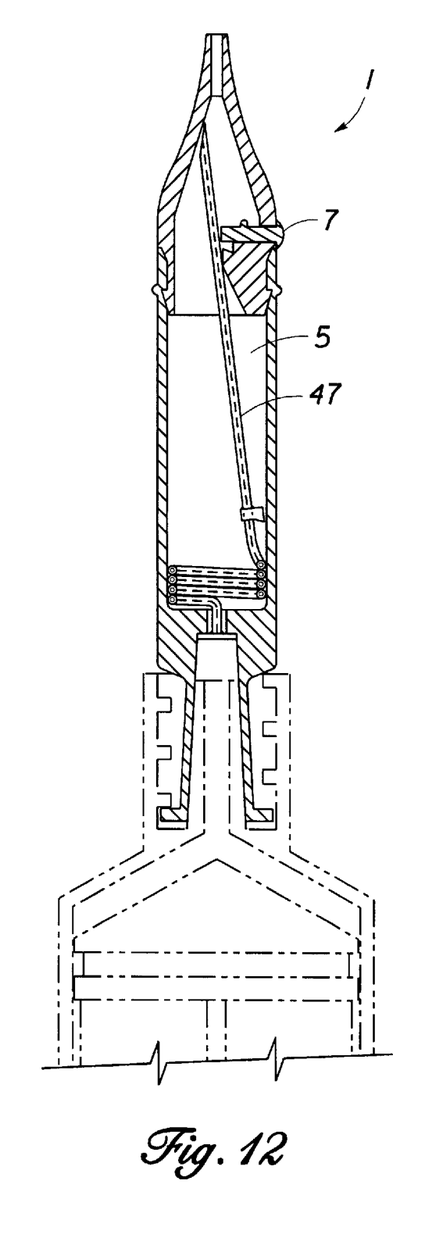
FIG. 12  Is a section elevation view of the spring needle cannula of FIG. 11 being retracted into the hub chamber.

Referring to FIG. 12 there is shown a section elevation of the biased spring needle cannula 47 after it has been used.

The cannula cap has been removed, the distal end of the biased spring needle cannula has penetrated the skin or outer layer of a body and medicament has been injected into said body and the cannula release button 7 has been pressed thus releasing the biased spring needle cannula 47 to be contained in the hub chamber 5.

Although the system described in detail supra has been found to be most satisfactory and preferred, many varriations are possible. For example a slip on hub could be used and a cap could be placed over the cannula distal end and the cannula release button.

Although the invention has been described with reference to the preferred embodiment, it would be understood by those skilled in the art, that additions, modifications, substitutions, deletions, and other changes not specificaly described may be made in the embodiments herein, it should be understood that the details herein are to be interpreted as illustrative and are not in a limiting sense.

What is claimed as invention is:

1. A modular assembly device that is fixed to a syringe and can be removed from a syringe wherein said modular assembly device is used as a skin penetrating conduit for injecting medicament or fluid from said syringe into a body, the modular assembly device comprising:

a threaded flange with a first side and a second side;

a hub with a first end and a second end, wherein said second end of said hub is fixed to said first side of said threaded flange;

a hub chamber with a first end and a second end wherein said hub chamber has an inside and an outside and wherein said hub chamber is hollow and wherein said second end of said hub chamber is integral with said first end of said hub;

a hub chamber cap with a first end and a second end and wherein said hub chamber cap has a hole formed near said second end of said hub chamber cap and wherein said hub chamber cap is hollow with an inside and outside and wherein said second end of said hub chamber cap is fixed to said first end of said hub chamber and wherein said hub chamber cap has hub tunnel formed in said first end of said hub chamber cap and wherein said hub tunnel extends from said first end of said hub chamber cap toward said second end of said hub chamber cap;

a latch having a first end and a second end and wherein said first end of said latch is integral with said inside surface of said hub chamber cap and wherein an inclined plane is formed on said second end of said latch;

a cannula release button with a first end and a second end and wherein a first knob is formed on said first end of said cannula release button and a second knob is formed between said first end and second end of said cannula release button and said cannula release button is disposed in said hub chamber cap hole formed in said hub chamber cap;

a biased spring needle cannula with a distal end and a proximal end wherein said proximal end is fixed to said second end of said hub chamber and wherein said distal end of said biased spring needle cannula is disposed in said hub tunnel formed in said hub chamber cap and said distal end of said biased spring needle cannula extends past said hub tunnel formed in said hub chamber cap and wherein coils are formed between said distal end and said proximal end of said biased spring needle cannula forming a spring in said biased spring needle cannula;

a cannula push out hook with a first side, a second side, a third side, and a fourth side and wherein a hole is formed in said cannula push out hook wherein said hole extends from said first side to said second side and wherein said biased spring needle cannula is disposed in said hole formed in said cannula push out hook and wherein said cannula push out hook is fixed to said biased spring needle cannula and wherein said third side of said cannula push out hook has an inclined plane formed that will correspond with said latch inclined plane and wherein said push out hook inclined plane is hooked onto said latch inclined plane thereby preventing a said distal end of said biased spring needle cannula from retreating or being pulled into said hub chamber by said coils and wherein after said biased spring needle cannula has been used to inject medicament into a body said first knob on said cannula release button is pressed with a finger or a thumb and wherein said second end of said cannula release button is thrust against said fourth side of said cannula push out hook thereby pushing said cannula push out hook away and out of said latch inclined plane thereby disengaging said latch inclined plane from said push out hook inclined plane and thereby allowing said biased coils formed on said biased spring needle cannula to pull said distal end of said spring needle cannula into said hub chamber and said hub chamber cap thereby preventing said distal end of said biased spring needle cannula from being exposed or from falling out of said hub chamber or said hub tunnel formed in said hub chamber cap.

2. The modular assemmbly device of claim 1 wherein said hub is a slip on hub.

3. The modular assembly device of claim 1 wherein said biased spring needle cannula forms a spring that holds said cannula push out hook in said incline plane latch.

4. The modular assembly device of claim 1 wherein said cannula push out hook engages the latch to allow said first end of said biased spring needle cannula to be thrust into a body without any movement of the biased spring needle cannula in the direction of said hub.

5. A composite needle cannula module comprising:
a hub chamber,
a rigid needle cannula having a first end extending from the hub chamber and a second end;
a biased spring cannula within the hub chamber, the spring cannula having a first end fixed to said second end of said rigid needle cannula and a second end fixed to said hub chamber.

6. The composite needle cannula module of claim 5 wherein said spring cannula is made out of metal.

7. The composite needle cannula module of claim 5 wherein said spring cannula is made out of plastic.

8. A modular needle assembly for use with a conventional syringe, comprising:
(a) a hub chamber comprising a first end having a hub tunnel therethrough and a second end having a hub for connecting to the conventional syringe;
(b) a biased spring needle cannula having a distal end extending through the hub tunnel and a proximal end fixed to the hub for the transfer of medicament from the syringe;
(c) a latch formed on the inside of the hub chamber preventing the distal end of the needle cannula from being pulled into the hub chamber; and
(d) a latch release button extending through a hole in the hub chamber near the latch for disengaging the latching means.

9. The modular needle assembly of claim 8, wherein the spring needle cannula is coiled.

10. The modular needle assembly of claim 8, wherein the latch is an inclined plane latch.

11. The modular needle assembly of claim 8, wherein the hub is connectable with a conventional syringe tip selected from a luer-lok tip, a slip tip, an eccentric tip and a catheter tip.

12. The modular needle assembly of claim 8, wherein the spring needle cannula has a hook adjacent the distal end of the spring needle cannula inside the chamber, and wherein the latch engages the hook.

13. The modular needle assembly of claim 8, wherein releasing the latch causes the distal end of the needle cannula to be pulled into the hub chamber by the biased spring needle cannula.

14. A composite needle cannula, comprising:
a skin penetration cannula portion made from a first material and having a proximal end; and
a second cannula portion permanently affixed to the proximal end of the skin penetration cannula, wherein the second cannula portion is made from a second material that is different from the first material, and wherein the second cannula portion is a spring cannula.

15. The composite needle cannula of claim 14, wherein the first and second materials are different grades of steel.

16. The composite needle cannula of claim 14, wherein the first material is steel and the second material is plastic.

17. The composite needle cannula of claim 14, wherein the first material is rigid and the second material is resilient.

18. The composite needle cannula of claim 14, wherein the spring cannula portion has a greater diameter than the skin penetration cannula portion.

19. A composite needle cannula, comprising:
- a first end of the composite needle cannula comprising a skin penetration cannula made from a first material; and
- a second end of the composite needle cannula made from a second material that is different than the first material, wherein the first end of the composite needle cannula is permanently fixed to the second end of the composite needle cannula, and wherein the second cannula portion of the composite needle cannula is a spring cannula.

20. The composite needle cannula of claim 19, wherein the first material is steel and the second material is plastic.

21. The composite needle cannula of claim 19, wherein the second cannula portion has a greater diameter than the first cannula portion.

22. The composite needle cannula of claim 19, wherein the second cannula portion is made to avoid crimping.

23. The cannula of claim 14, wherein the skin penetration cannula portion and the second cannula portion are not positioned in an embedded or nested relationship.

24. A composite needle cannula, comprising:
- a first end of the composite needle cannula comprising a skin penetration cannula made from a first material; and
- a second end of the composite needle cannula made from a second material that is different than the first material, wherein the first end of the composite needle cannula is permanently fixed to the second end of the composite needle cannula, and wherein the skin penetration cannula portion is fixed in series with the second cannula portion, and wherein the second cannula portion is a spring cannula.

* * * * *